United States Patent [19]

Isobe et al.

[11] Patent Number: 5,094,840

[45] Date of Patent: Mar. 10, 1992

[54] FOAMABLE DENTIFRICE COMPOSITION

[75] Inventors: Kenji Isobe, Chiba; Nobuyuki Miyajima, Tokyo; Hiroshi Yutani, Narashino, all of Japan

[73] Assignee: Lion Corporation, Tokyo, Japan

[21] Appl. No.: 600,984

[22] Filed: Oct. 23, 1990

[30] Foreign Application Priority Data

Oct. 31, 1989 [JP] Japan ................... 1-281858

[51] Int. Cl.$^5$ ............... A61K 7/16; A61K 7/28
[52] U.S. Cl. ........................ 424/50; 414/49
[58] Field of Search ................. 424/49-58

[56] References Cited

U.S. PATENT DOCUMENTS

| | | | |
|---|---|---|---|
| 3,919,409 | 11/1975 | Perla et al. | 424/52 |
| 3,928,555 | 12/1975 | Gault | 424/49 |
| 4,711,902 | 12/1987 | Serno | 514/937 |

*Primary Examiner*—Shep K. Rose
*Attorney, Agent, or Firm*—Wenderoth, Lind & Ponack

[57] ABSTRACT

A novel foaming agent in dentifrice compositions, e.g., tooth pastes, is proposed which is an at least partially, with a basic compound, neutralized salt of a glycerin diester compound represented by the general formula $$R^1-CO-O-CH_2-CHOH-CH_2-O-CO-R^2,$$

in which $R^1-CO-$ is a residue of a monobasic carboxylic acid having 8 to 18 carbon atoms in a molecule, e.g., lauric acid, and $R^2$ is a residue of a polybasic carboxylic acid, e.g., succinic acid, from which one of the carboxyl groups is eliminated of which is a 1% by weight aqueous solution has a pH value in the range from 4 to 10 at 25° C. The dentifrice composition compounded with 0.1-10% by weight of the above defined foaming agent has outstandingly high foamability and is advantageous in respect of the little adverse influences on the stability of enzymes contained in the dentrifices composition.

10 Claims, No Drawings

1

FOAMABLE DENTIFRICE COMPOSITION

BACKGROUND OF THE INVENTION

The present invention relates to a novel foamable dentifrice composition or, more particularly, to a foamable dentifrice composition containing a unique foaming ingredient for use in cleaning of oral cavities and teeth.

It is conventional that dentifrice compositions such as tooth pastes are formulated with a surface active agent with an object to enhance the cleaning effect for removal of filths in the oral cavity or on teeth. The surface active agent compounded in dentifrice compositions must satisfy various requirements, in addition to the above mentioned cleaning effect as a matter of course, such as adequate foamability, absence of any unpleasant odor or taste, fresh feeling given to the user of the dentifrice, absolute absence of toxicity and irritativeness and the like.

Conventional surface active agents widely used as an ingredient of dentifrice compositions are mostly anionic ones such as sodium lauryl sulfate which, however, has problems that the inducing effect is insufficient and the stability of the enzymes sometimes formulated in dentifrice compositions is decreased thereby.

Non-ionic surface active agents, such as sucrose fatty acid esters and polyglycerin fatty acid esters, are also under use for the same purpose but they are generally inferior in respect of the foamability of the composition as compared with anionic surface active agents though superior thereto in respect of the less adverse influences on the stability of enzymes.

Thus, it is eagerly desired to develop a dentifrice composition having excellent foamability and juicing effect without adverse influences on the stability of enzymes contained therein by overcoming the above mentioned problems and disadvantages in the prior art compositions compounded with conventional surface active agents.

SUMMARY OF THE INVENTION

The present invention accordingly has an object to provide a novel dentifrice composition having excellent foamability and juicing effect without adverse influences on the stability of enzymes contained therein by using a unique surface active foaming agent which could overcome the above mentioned problems and disadvantages in the prior art compositions compounded with conventional surface active agents. The invention also has an object of imparting a dentifrice composition with adequate foamability without any adverse influences on the stability of the enzymes contained in the composition.

Thus, the foamable dentifrice composition of the invention comprises:

from 0.1 to 10% by weight of a foaming agent which is an at least partially neutralized salt of a glycerin diester compound represented by the general formula

in which $R^1$—CO— is a residue of a monobasic carboxylic acid having 8 to 18 carbon atoms in a molecule and $R^2$ is a residue of a polybasic carboxylic acid from which one of the carboxyl groups is eliminated, a 1% by weight aqueous solution thereof having a pH value in the range from 4 to 10 at 25° C., the balance of the composition being known ingredients of dentifrice compositions.

The method of the invention accordingly comprises: uniformly admixing a dentifrice composition with the foaming agent defined above in an amount in the range from 0.1 to 10% by weight based on the total amount of the dentifrice composition after admixture of the foaming agent.

DETAILED DESCRIPTION OF THE PREFERRED EMBODIMENTS

As is described above, the most characteristic feature of the inventive dentifrice composition consists in the admixture of the unique foaming agent which is an at least partially neutralized product of the compound represented by the above given general formula (I).

The compound represented by the general formula (I) is a known compound and is used, for example, as a food additive (see, for example, Japanese Patent Kokai 59-42853). This compound, however, is oil-soluble with low hydrophilicity so that it cannot be compounded as such in a dentifrice composition. The at least partially neutralized salt of the compound represented by the general formula (I) can be prepared, for example, in the following manner.

The starting material in the preparation thereof is a monoglyceride compound represented by the general formula

in which $R^1$—CO— has the same meaning as defined above, is mixed with a polybasic carboxylic acid represented by the general formula

in which $R^2$ has the same meaning as defined above, or an anhydride thereof and they are heated and melted, if necessary, with admixture of a small amount of a basic compound as a catalyst to effect an esterification reaction for forming the compound of the general formula (I) which is converted to a salt by neutralization thereof with an alkaline compound according to a known procedure. Since the polybasic carboxylic acid of the general formula (III) has at least two free carboxyl groups in a molecule and only one of them is esterified, the compound of the general formula (I) has at least one carboxyl group in a molecule. It is optional whether all of these carboxyl groups are neutralized or only a part of the carboxyl groups are neutralized so that the partial neutralization product is a mixture of the unneutralized acid and a salt formed by neutralization. It is preferable that, in place of the polybasic carboxylic acid of the general formula (III), an anhydride derived from the acid is used in the esterification reaction with the monoglyceride of the general formula (II) because the reaction proceeds more rapidly at a lower temperature than with the corresponding polybasic carboxylic acid per se. For example, the esterification reaction between a monoglyceride compound and succinic anhydride is complete usually within 90 minutes at a temperature of about 130° C. while the reaction with succinic acid usually takes 120 minutes or longer at a temperature of 150° C. If necessary, the esterification reaction is performed under an atmosphere of an inert gas in order to prevent discoloration of the reaction product or occurrence of unpleasant odor or taste therein. The reaction mixture after completion of the reaction still contains a substantial amount of the starting monoglyceride compound as unreacted, which may have an adverse effect on the foamability of the composition when the content thereof is large. Accordingly, it is preferable that the reaction mixture after completion of the reaction is subjected to a purification treatment by a process of solvent extraction or other suitable means to remove the unreacted monoglyceride compound.

The acyl group represented by $R^1$—CO— in the above given general formula (II) is necessarily a residue of a monobasic carboxylic acid $R^1$—CO—OH having from 8 to 18 carbon atoms in a molecule. When the number of carbon atoms in the acyl group is smaller than 8, the foaming agent prepared from such a monoglyceride compound cannot impart the dentifrice composition with full foamability along with an adverse influence on the taste of the dentifrice composition. When the number of carbon atoms in the acyl group is larger than 18, the esterification product of the monoglyceride compound with the polybasic carboxylic acid or salt thereof is less water-soluble not to give sufficient foamability to the composition compounded therewith. The monobasic carboxylic acid of the formula $R^1$—CO—OH, from which the monoglyceride compound of the general formula (II) is derived, can be saturated or unsaturated and straightly linear or branched in the molecular structure and is exemplified by caprylic acid, capric acid, lauric acid, myristic acid, palmitic acid, stearic acid, isostearic acid, oleic acid and the like though not particularly limitative thereto.

The monoglyceride compound of the general formula (II) is prepared either by a chemical synthetic method or by an enzymatic method and can be used regardless of the origin. It should be noted that the monoglyceride product should contain the diglyceride and triglyceride compounds as the by-products in as small as possible amounts because an excessively large amount of these by-products may have an adverse influence on the foamability of the dentifrice composition compounded with the foaming agent derived from the monoglyceride compound. It is preferable, if necessary, that the monoglyceride product is subjected to a purification treatment prior to use although commercial supply is available in recent years of the monoglyceride products after purification by molecular distillation to be usable without further purification.

The polybasic carboxylic acid of the above given general formula (III) with which or with an anhydride of which the above described monoglyceride compound is reacted is not particularly limitative provided that the molecule thereof has at least two carboxyl groups. Examples of suitable polybasic carboxylic acid include malic acid, citric acid, succinic acid, maleic acid, glutaric acid, adipic acid, malonic acid, tartaric acid, diacetyl tartaric acid and the like though not particularly limitative thereto. The anhydrides of these polybasic acids of course can be used as the esterifying agent of the monoglyceride compound. Particularly preferable among the above named polybasic carboxylic acids and anhydrides thereof are succinic acid, succinic anhydride, citric acid, tartaric acid, diacetyl tartaric acid, glutaric acid and glutaric anhydride.

It is usual in the esterification reaction of the monoglyceride compound of the general formula (II) with the polybasic carboxylic acid of the general formula (III) or an anhydride thereof that a position isomer of the compound of the general formula (I), in which the hydroxy group at the 2-position, instead of the 3-position, of the glycerin structure is esterified, and the full esterification product, in which the hydroxy groups at the 2- and 3-positions are both esterified, are produced in small amounts as the by-products. These by-product esterification products need not be removed and the esterification product containing them can be used as such.

The thus obtained esterification product of the general formula (I) is neutralized partially or fully by using a basic compound as the neutralizing agent which can be any of inorganic and organic bases. Examples of suitable inorganic basic compound include, for example, sodium hydroxide, potassium hydroxide, sodium carbonate, potassium carbonate, sodium hydrogen carbonate, potassium hydrogen carbonate and the like. Examples of suitable organic basic compound include, for example, monoethanolamine, diethanolamine, triethanolamine, monopropanolamine, dipropanolamine and the like. The degree of neutralization should be controlled so that a 1% by weight aqueous solution of the neutralization product may have a pH value in the range from 4 to 10 or, preferably, from 6 to 9.5 at 25° C. When neutralization is complete, the neutralized product gives a pH of 9 to 10. A pH value of the neutralized product higher than 10 means that the product contains a free alkali so that the dentifrice composition compounded with such an overly neutralized salt is undesirable with unpleasant taste due to the free alkali.

It is optional according to need to use the partial or full neutraliation products of two kinds or more of the compounds of the general formula (I) in combination as the foaming agent. The amount of the foaming agent in the dentifrice composition of the invention is in the range from 0.1 to 10% by weight or, preferably, from 0.5 to 5% by weight based on the overall amount of the composition depending on the type of the dentifrice composition and the desired foamability to meet the preference of the users. The dentifrice composition of the invention containing the above described unique foaming agent is imparted with adequate foamability to exhibit an excellent cleaning effect on oral cavities and on teeth with no adverse influences on the stability of enzymes contained therein along with very fresh feeling given to the users of the composition.

The ingredients of the inventive dentifrice composition other than the above described foaming agent are not limitative and can be selected from those conventionally used in dentifrice compositions in general. Examples of the substances as the ingredients of the inventive dentifrice composition include surface active agents such as alkyl sulfates, N-acyl taurates, sucrose fatty acid esters, polyglycerin fatty acid esters, polyoxyethylene sorbitan fatty acid esters and the like, polishing agents such as calcium hydrogen phosphate, calcium carbonate, anhydrous silicic acid and the like, thickening agents such as glycerin, sorbitol, propylene glycol, polyethylene glycol and the like, binding agents such as carboxymethyl cellulose, carrageenan, sodium alginate, hydroxyethyl cellulose, polyvinyl alcohol and the like, sweetening agents, flavors, coloring agents, germicides, enzymes, anti-inflammatory agents, stabilizers and so on.

In the following, examples are given to illustrate the advantages obtained with the inventive dentifrice composition in more detail but not to limit the scope of the invention in any way.

EXAMPLE 1

Foaming agents as a neutralization product of the monoglyceride compound of the general formula (I) were prepared in the following manner.

Preparation 1

Into a three necked flask of 300 ml capacity equipped with a stirrer and a thermometer were introduced 100 g of a commercial product of lauroyl monoglyceride (Sunsoft No. 750, a product by Taiyo Kagaku Co.) which was melted by heating. After complete melting of the monoglyceride, 36.5 g of succinic anhydride were added to the monoglyceride melt and the mixture was heated at 130° C. for 1.5 hours with agitation under a stream of nitrogen gas followed by cooling. The thus obtained white semi-solid product was the desired succinic acid ester of the lauroyl monoglyceride and had an acid value of 150 mg KOH/g. The succinic acid ester was neutralized with a different amount of a 1% by weight aqueous solution of sodium hydroxide to give six kinds of at least partially neutralization products of which 1% by weight aqueous solutions had pH values of 3.5, 4.5, 6, 7, 9 and 10 at 25° C. These neutralization products are referred to hereinbelow as the foaming agents Ia, Ib, Ic, Id, Ie and If, respectively.

Preparation 2

A commercial product of lauroyl monoglyceride (Poem M-300, a product by Riken Vitamin Co.) was esterified with glutaric anhydride in substantially the same manner as in Preparation 1 described above to give a glutaric acid ester of lauroyl monoglyceride in the form of a crude product. The crude product was completely neutralized with a 5% aqueous solution of sodium hydrogen carbonate followed by extraction of the aqueous solution with diethyl ether to remove the unreacted lauroyl monoglyceride as an extract in the ether. The aqueous solution after extraction was acidified by adding diluted hydrochloric acid to have a pH of 3 and then subjected to extraction with chloroform so as to transfer the glutaric acid ester of lauroyl monoglyceride into a chloroform solution from which chloroform as the solvent was removed by evaporation to give the glutaric acid ester of lauroyl monoglyceride in a purified form. The glutaric acid ester of lauroyl monoglyceride thus purified was neutralized with a 1% by weight aqueous solution of sodium hydroxide followed by concentration to give a salt, referred to as the foaming agent II herein-below, of which a 1% by weight aqueous solution had a pH of 8 at 25° C.

Preparation 3

A commercial product of decanoyl monoglyceride (Sunsoft No. 760, a product by Taiyo Kagaku Co.) was esterified with an equimolar amount of succinic anhydride in substantially the same manner as in Preparation 1 described above to give a succinic acid ester of decanoyl monoglyceride which was neutralized with a 1% by weight aqueous solution of sodium hydroxide to give a salt of the succinic acid ester of decanoyl monoglyceride, referred to as the foaming agent III herein-below, of which a 1% by weight aqueous solution had a pH of 7 at 25° C.

Preparation 4

A commercial product of myristoyl monoglyceride (Sunsoft No. 8002, a product by Taiyo Kagaku Co.) was esterified with an equimolar amount of succinic anhydride in substantially the same manner as in Preparation 1 described above to give a succinic acid ester of myristoyl monoglyceride which was neutralized with a 1% by weight aqueous solution of sodium hydroxide to give a salt of the succinic acid ester of myristoyl monoglyceride, referred to as the foaming agent IV hereinbelow, of which a 1% by weight aqueous solution had a pH of 8 at 25° C.

Tooth paste compositions were prepared each in the following formulation, of which the foaming agent was either one of the foaming agents prepared in preparations 1 to 4 described above.

| Tooth paste composition | |
|---|---|
| Calcium monohydrogen phosphate | 45.0% by weight |
| Anhydrous silicic acid | 3.0 |
| Sodium carboxymethyl cellulose | 0.8 |
| Carrageenan | 0.2 |
| Sorbitol fluid | 26.0 |
| Propylene glycol | 3.0 |
| Sodium saccharin | 0.2 |
| Perfume | 1.0 |
| Foraming agent | 2.0 |
| Antiseptics | 0.1 |
| Purified water | balance |
| Total | 100.0 |

The foaming power of these tooth paste compositions was evaluated in the following manner. Thus, a 1 g portion of the tooth paste composition containing one of the foaming agents prepared in Preparations according to the above given formulation was dissolved and dispersed at 25° C. in 20 ml of deionized water in an Epton tube of 100 ml capacity which was vigorously shaken up and down 20 times within 10 seconds and kept standing for 5 minutes to record the volume of the foams on the liquid layer as a measure of the foaming power. The results are shown in the table given below. For comparison, three more tooth pate compositions were prepared in the same formulation as above excepting replacement of the foaming agent prepared in Preparations with the same compound prepared in Preparation 1 but without neutralization, referred to as the unneutralized foaming agent hereinbelow, and a commercial product of sucrose monolaurate or decaglycerin monolaurate.

| Foaming agent | Foam volume, ml |
|---|---|
| Inventive Example | |
| Foaming agent Ib (pH = 4.5) | 45 |
| Foaming agent Ic (pH = 6) | 52 |
| Foaming agent Id (pH = 7) | 54 |
| Foaming agent Ie (pH = 9) | 56 |
| Foaming agent If (pH = 10) | 56 |
| Foaming agent II (pH = 8) | 46 |
| Foaming agent III (pH = 7) | 45 |
| Foaming agent IV (pH = 8) | 48 |
| Comparative Example | |
| Unneutralized foaming agent | 25 |
| Foaming agent Ia (pH = 3.5) | 30 |
| Sucrose monolaurate | 33 |
| Decaglycerin monolaurate | 22 |

As is clear from the above given results, the tooth paste compositions according to the invention have a foaming power much higher than that of the comparative tooth paste compositions containing a conventional foaming agent and that the limitation of the pH value, which a 1% aqueous solution of the foaming agent used in the inventive dentifrice composition should have at 25° C., is a very critical parameter for the foaming power of the composition.

EXAMPLE 2

Four more tooth paste compositions were prepared in the same formulation as in Example 1 except that the amount of the foaming agent, which was the foaming agent Ic prepared in Preparation 1, was varied between 0.5 and 5% by weight with corresponding modification in the amount of the purified water. The results of the foaming test were as follows.

| Foaming agent, % by weight | Foam volume, ml |
| --- | --- |
| 0.5 | 35 |
| 1.0 | 42 |
| 3.0 | 62 |
| 5.0 | 70 |

As is clear from the above shown results, the foaming power of the tooth paste composition can be freely controlled by adjusting the amount of the foaming agent to comply with the user's preference. Incidentally, the foaming power of a tooth paste corresponding to the foam volume larger than 70 ml in the above mentioned test rarely meets the preference of most users.

EXAMPLE 3

An enzyme solution was prepared by dissolving 0.3 g of dextranase having an activity of 1,200,000 units per g in 100 ml of a 10 mM phosphate buffer solution having a pH of 7.0. A 1 ml portion of this enzyme solution was admixed with 19 ml of an aqueous solution of a surface active agent shown below in the indicated concentration and the solution was kept standing at 40° C. for 1 hour. Thereafter, a 0.5 ml portion of the solution was taken and admixed with 2 ml of a 2.5% by weight aqueous solution of dextran and kept for 10 minutes at 40° C. to effect enzymatic decomposition of dextran. The reducing sugar isolated by this enzymatic decomposition of dextran was determined by the Somogyi's method to give the results shown below as a measure of the enzymatic activity of the dextranase. The results below are given in the relative value taking the activity in the control test, in which no surface active agent was added, as 100%.

| Surface active agent (concentration, % by weight) | Relative activity, % |
| --- | --- |
| None (control) | 100 |
| Foaming agent Id (0.5) | 98 |
| Foaming agent Id (1.0) | 97 |
| Foaming agent Id (2.0) | 95 |
| Sodium lauryl sulfate (1.0) | 0 |
| Sodium N-lauroylsarcosine (1.0) | 67 |
| Sodium lauryl sulfate (1.0) + lauric acid diethanolamide (2.0) | 80 |
| Sodium lauryl sulfate (1.0) + sucrose ester of hardened beef tallow fatty acid (2.0) | 78 |

As is clear from the above given results, the foaming agent used in the inventive dentifrice composition has little influences on the stability of dextranase. In this regard, the foaming agent is even more advantageous than the surface active agents conventionally used in dentifrice compositions with preference due to the relatively small adverse influences on the activity of enzymes.

What is claimed is:

1. A foamable enzyme-containing dentifrice composition which comprises: from 0.1 to 10% by weight of a foaming agent which is an at least partially, with a basic compound, neutralized salt of a glycerin diester compound represented by the general formula $$R^1-CO-O-CH_2-CHOH-CH_2-O-CO-R^2,$$

in which $R^1-CO-$ is a residue of a monobasic carboxylic acid having 8 to 18 carbon atoms in a molecule and $R^2$ is a residue of a polybasic carboxylic acid from which one of the carboxyl groups is eliminated, a 1% by weight aqueous solution thereof having a pH value in the range from 4 to 10 at 25° C., the balance of the composition being dentifrice adjuvants.

2. The foamable dentifrice composition as claimed in claim 1 in which the monobasic carboxylic acid, from which the residue of the formula $R^1-CO-$ is derived, is selected from the group consisting of caprylic acid, capric acid, lauric acid, myristic acid, palmitic acid, stearic acid, isostearic acid and oleic acid.

3. The foamable dentifrice composition as claimed in claim 1 in which the polybasic carboxylic acid, from which the residue of the formula $R^2$ is derived, is selected from the group consisting of succinic acid, citric acid, tartaric acid, diacetyl tartaric acid and glutaric acid.

4. The foamable dentifrice composition as claimed in claim 1 in which a 1% by weight aqueous solution of the at least partially neutralized salt of the glycerin diester compound has a pH value in the range from 6 to 9.5 at 25° C.

5. The foamable dentifrice composition as claimed in claim 1 in which the amount of the foaming agent is in the range from 0.5 to 5% by weight based on the overall amount of the dentifrice composition.

6. A method for imparting an enzyme-containing dentifrice composition with foamability which comprises:
uniformly admixing the dentifrice composition with a foaming agent which is an at least partially, with a basic compound, neutralized salt of a glycerin diester compound represented by the general formula $$R^1-CO-O-CH_2-CHOH-CH_2-O-CO-R^2,$$

in which $R^1-CO-$ is a residue of a monobasic carboxylic acid having 8 to 18 carbon atoms in a molecule and $R^2$ is a residue of a polybasic carboxylic acid from which one of the carboxyl groups is eliminated, a 1% by weight aqueous solution thereof having a pH value in the range from 4 to 10 at 25° C., in an amount in the range from 0.1 to 10% by weight based on the overall amount of the dentifrice composition after admixture of the foaming agent.

7. The method for imparting a dentifrice composition with foamability as claimed in claim 6 in which the monobasic carboxylic acid, from which the residue of the formula $R^1-CO-$ is derived, is selected from the group consisting of caprylic acid, capric acid, lauric acid, myristic acid, palmitic acid, stearic acid, isostearic acid and oleic acid.

8. The method for imparting a dentifrice composition with foamability as claimed in claim 6 in which the polybasic carboxylic acid, from which the residue of the formula $R^2$ is derived, is selected from the group consisting of succinic acid, citric acid, tartaric acid, diacetyl tartaric acid and glutaric acid.

9. The method for imparting a dentifrice composition with foamability as claimed in claim 6 in which a 1% by weight aqueous solution of the at least partially neutralized glycerin diester compound has a pH value in the range from 6 to 9.5 at 25° C.

10. The method for imparting a dentifrice composition with foamability as claimed in claim 6 in which the amount of the foaming agent is in the range from 0.5 to 5% by weight based on the overall amount of the dentifrice composition.

* * * * *